United States Patent
Voros et al.

(10) Patent No.: US 10,130,274 B2
(45) Date of Patent: Nov. 20, 2018

(54) PDMS-BASED STRETCHABLE MULTI-ELECTRODE AND CHEMOTRODE ARRAY FOR EPIDURAL AND SUBDURAL NEURONAL RECORDING, ELECTRICAL STIMULATION AND DRUG DELIVERY

(75) Inventors: Janos Voros, Zurich (CH); Gregoire Courtine, Zurich (CH); Alexandre Larmagnac, Zurich (CH); Pavel Musienko, Zurich (CH)

(73) Assignee: Ecole Polytechnique Federale De Lausanne (EPFL), Lausanne (CH)

( * ) Notice: Subject to any disclaimer, the term of this patent is extended or adjusted under 35 U.S.C. 154(b) by 1329 days.

(21) Appl. No.: 13/704,420

(22) PCT Filed: Jun. 14, 2011

(86) PCT No.: PCT/EP2011/059855
§ 371 (c)(1),
(2), (4) Date: Jul. 5, 2013

(87) PCT Pub. No.: WO2011/157714
PCT Pub. Date: Dec. 22, 2011

(65) Prior Publication Data
US 2013/0303873 A1    Nov. 14, 2013

(30) Foreign Application Priority Data

Jun. 15, 2010    (EP) .................................... 10006195

(51) Int. Cl.
*A61B 5/04*    (2006.01)
*A61N 1/05*    (2006.01)
(Continued)

(52) U.S. Cl.
CPC .......... *A61B 5/04001* (2013.01); *A61B 5/407* (2013.01); *A61N 1/0551* (2013.01);
(Continued)

(58) Field of Classification Search
CPC . A61B 5/04001; A61B 5/4029–5/4052; A61B 5/4058–5/407; A61B 5/6868;
(Continued)

(56) References Cited

U.S. PATENT DOCUMENTS 7,146,221 B2    12/2006  Krulevitch et al.
2004/0121528 A1*   6/2004  Krulevitch ........... A61N 1/0452
                                                438/166
(Continued)

FOREIGN PATENT DOCUMENTS

WO    2007047852 A2    4/2007

OTHER PUBLICATIONS

Axisa et al., Elastic and Conformable Electronic Circuits and Assemblies using MID in polymer, 6th International Conference on Polymers and Adhesives in Microelectronics and Photonics, IEEE Polytronic 2007 Conference, Jan. 1, 2007, pp. 280-286.
(Continued)

*Primary Examiner* — Lee S Cohen
*Assistant Examiner* — Erin M Cardinal
(74) *Attorney, Agent, or Firm* — McCoy Russell LLP

(57) ABSTRACT

An implantable device for the electrical and/or pharmaceutical stimulation of the central nervous system, especially the spinal cord, is suggested. The device comprises a conformable substrate which is primarily composed of a flexible and stretchable polymer, and a plurality of flexible electrodes and conductive leads embedded in the conformable substrate. Not only the substrate, but also the leads are stretchable. The substrate may consist of PDMS, and the leads may consist of a conductive PDMS, in particular, PDMS with an electrically conductive filler material, and may optionally be metal-coated. The device defines a multi-electrode array which may be employed for neurostimulation in the epidural or subdural space of an animal or human.

15 Claims, 11 Drawing Sheets

(51) Int. Cl.
    *H05K 1/02*     (2006.01)
    *A61N 1/30*     (2006.01)
    *B05D 7/00*     (2006.01)
    *A61B 5/00*     (2006.01)
    *H05K 1/09*     (2006.01)
    *H05K 3/12*     (2006.01)
    *H05K 3/24*     (2006.01)
    *H05K 3/46*     (2006.01)

(52) U.S. Cl.
    CPC .............. *A61N 1/303* (2013.01); *B05D 7/00* (2013.01); *H05K 1/0283* (2013.01); *A61B 2562/0215* (2017.08); *A61B 2562/046* (2013.01); *A61B 2562/125* (2013.01); *A61B 2562/164* (2013.01); *A61B 2562/166* (2013.01); *H05K 1/0272* (2013.01); *H05K 1/095* (2013.01); *H05K 3/1233* (2013.01); *H05K 3/246* (2013.01); *H05K 3/4664* (2013.01); *H05K 3/4682* (2013.01); *H05K 2201/0162* (2013.01); *H05K 2201/0329* (2013.01); *H05K 2203/016* (2013.01)

(58) Field of Classification Search
    CPC ............ A61B 5/6877; A61B 2562/164; A61N 1/0551; A61N 1/04; A61N 1/05
    See application file for complete search history.

(56) References Cited

U.S. PATENT DOCUMENTS

| | | | | |
|---|---|---|---|---|
| 2004/0192082 | A1* | 9/2004 | Wagner | H05K 1/0283 439/67 |
| 2004/0243204 | A1* | 12/2004 | Maghribi | A61N 1/05 607/115 |
| 2007/0004567 | A1 | 1/2007 | Shetty et al. | |
| 2007/0142878 | A1 | 6/2007 | Krulevitch et al. | |
| 2010/0087782 | A1* | 4/2010 | Ghaffari | A61B 1/00082 604/103.01 |
| 2010/0116526 | A1* | 5/2010 | Arora | H01L 23/4985 174/254 |
| 2011/0034912 | A1* | 2/2011 | de Graff | A61B 1/05 606/21 |
| 2011/0230747 | A1* | 9/2011 | Rogers | A61B 5/05 600/377 |
| 2011/0237921 | A1* | 9/2011 | Askin, III | A61B 5/0408 600/377 |

OTHER PUBLICATIONS

Courtine et al., Transformation of nonfunctional spinal circuits into functional states after the loss of brain input, Nature Neuroscience, Oct. 2009, pp. 1333-1344, vol. 12, No. 10.

Graf et al., Electrochemically Stimulated Release from Liposomes Enbedded in a Polyectrolyte Multilayer, Advanced Funtional Materials, 2011, pp. 1666-1672, vol. 21.

Lacour et al., Flexible and stretchable micro-electrodes for in vitro and in vivo neural interfaces, Med. Biol. Eng. Comput., 2010, pp. 945-954, vol. 48.

Lacour et al., Stretchable gold conductors on elastomeric substrates, Applied Physics Letters, Apr. 14, 2003, pp. 2404-2406, vol. 82, No. 15.

Musienko et al., Combinatory Electrical and Pharmacological Neuroprosthetic Interfaces to Regain Motor Function After Spinal Cord Injury, IEEE Transactions on Biomedical Engineering, Nov. 2009, pp. 2707-2711, vol. 56, No. 11.

Pellinen et al., Multifunctional Flexible Parylene-Based Intracortical Microelectrodes, Proceedings of the 2005 IEEE: Engineering in Medicine and Biology 27th Annual Conference, Sep. 1-4, 2005, pp. 5272-5275.

Wei et al., Stretchable microelectrode array using room-temperature liquid alloy interconnects, Journal of Micromechanics and Microengineering, 2011, pp. 1-8, vol. 21, No. 054015.

Ateh et al., "Polypyrrole-based Conducting Polymers and Interactions with Biological Tissues", Journal of the Royal Society Interface, Jun. 22, 2006, pp. 741-752, vol. 3.

Guyatt, G. et al., "The 6-minute walk: a new measure of exercise capacity in patients with chronic heart failure," Canadian Medical Association Journal, vol. 132, No. 8, Apr. 15, 1985, 5 pages.

Lovely, R. et al., "Effects of Training on the Recovery of Full-Weight-Bearing Stepping in the Adult Spinal Cat," Experimental Neurology, vol. 92, No. 2, May 1986, 15 pages.

Barbeau, H. et al., "Recovery of locomotion after chronic spinalization in the adult cat," Brain Research, vol. 412, No. 1, May 26, 1987, 12 pages.

Colgate, E. et al., "An Analysis of Contact Instability in Terms of Passive Physical Equivalents," Proceedings of the 1989 IEEE International Conference on Robotics and Automation, May 14, 1989, Scottsdale, Arizona, 6 pages.

Wernig, A. et al., "Laufband locomotion with body weight support improved walking in persons with severe spinal cord injuries," Paraplegia, vol. 30, No. 4, Apr. 1992, 10 pages.

Winter, D. et al., "An integrated EMG/biomechanical model of upper body balance and posture during human gait," Progress in Brain Research, vol. 97, Chapter 32, Available as Early as Jan. 1, 1993, 9 pages.

Wernig, A. et al., "Laufband Therapy Based on 'Rules of Spinal Locomotion' is Effective in Spinal Cord Injured Persons," European Journal of Neuroscience, vol. 7, No. 4, Apr. 1995, 7 pages.

Pratt, G. et al., "Stiffness Isn't Everything," Proceedings of the Fourth International Symposium on Experimental Robotics (ISER '95), Jun. 30, 1995, Stanford, California, 6 pages.

Basso, D. et al., "MASCIS Evaluation of Open Field Locomotor Scores: Effects of Experience and Teamwork on Reliability," Journal of Neurotrauma, vol. 13, No. 7, Jul. 1996, 17 pages.

Harkema, S. et al., "Human Lumbosacral Spinal Cord Interprets Loading During Stepping," Journal of Neurophysiology, vol. 77, No. 2, Feb. 1, 1997, 15 pages.

Brosamle, C. et al., "Cells of Origin, Course, and Termination Patterns of the Ventral, Uncrossed Component of the Mature Rat Corticospinal Tract," The Journal of Comparative Neurology, vol. 386, No. 2, Sep. 22, 1997, 11 pages.

Kakulas, B., "A Review of the Neuropathology of Human Spinal Cord Injury with Emphasis on Special Features," Proceedings of the Donald Munro Memorial Lecture at the American Paraplegia Society 44th Annual Conference, Sep. 9, 1998, Las Vegas, Nevada, 6 pages.

Hashtrudi-Zaad, K. et al., "On the Use of Local Force Feedback for Transparent Teleoperation," Proceedings of the 1999 IEEE International Conference on Robotics and Automation, May 10, 1999, Detroit, Michigan, 7 pages.

Kirkwood, P., "Neuronal Control of Locomotion: From Mollusc to Man—G.N. Orlovsky, T.G. Deliagina and S. Grinner. Oxford University Press, Oxford, 1999. ISBN 0198524056 (Hbk), 322 pp.," Clinical Neurophysiology, vol. 111, No. 8, Aug. 1, 2000, Published Online Jul. 17, 2000, 2 pages.

Pratt, J. et al., "Series elastic actuators for high fidelity force control," Industrial Robot: An International Journal, vol. 29, No. 3, Available as Early as Jan. 1, 2002, 13 pages.

Steward, O. et al. "False Resurrections: Distinguishing Regenerated from Spared Axons in the Injured Central Nervous System," The Journal of Comparative Neurology, vol. 459, No. 1, Apr. 21, 2003, 8 pages.

Pearson, K., "Generating the walking gait: role of sensory feedback," Progress in Brain Research, vol. 143, Chapter 12, Published Online Nov. 28, 2003, 7 pages.

Bareyre, F. et al., "The injured spinal cord spontaneously forms a new intraspinal circuit in adult rats," Nature Neuroscience, vol. 7, No. 3, Mar. 2004, Published Online Feb. 15, 2004, 9 pages.

Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, Mar. 15, 2004, 11 pages.

(56) References Cited

OTHER PUBLICATIONS

Liu, J. et al., "Stimulation of the Parapyramidal Region of the Neonatal Rat Brain Stem Produces Locomotor-Like Activity Involving Spinal 5-HT7 and 5-HT2A Receptors," Journal of Neurophysiology, vol. 94, No. 2, Aug. 1, 2005, Published Online May 4, 2005, 13 pages.
Timoszyk, W. et al., "Hindlimb loading determines stepping quantity and quality following spinal cord transection," Brain Research, vol. 1050, No. 1-2, Jul. 19, 2005, Published Online Jun. 24, 2005, 10 pages.
Wernig, A., "'Ineffectiveness' of Automated Locomotor Training," Archives of Physical Medicine and Rehabilitation, vol. 86, No. 12, Dec. 2005, 2 pages.
Nessler, J. et al., "A Robotic Device for Studying Rodent Locomotion After Spinal Cord Injury," IEEE Transactions on Neural Systems and Rehabilitation Engineering, vol. 13, No. 4, Dec. 12, 2005, 10 pages.
Reinkensmeyer, D. et al., "Tools for understanding and optimizing robotic gait training," Journal of Rehabilitation Research & Development, vol. 43, No. 5, Aug. 2006, 14 pages.
Frey, M. et al., "A Novel Mechatronic Body Weight Support System," IEEE Transactions on Neural Systems and Rehabilitation Engineering, vol. 14, No. 3, Sep. 18, 2006, 11 pages.
Cai, L. et al., "Implications of Assist-As-Needed Robotic Step Training after a Complete Spinal Cord Injury on Intrinsic Strategies of Motor Learning," The Journal of Neuroscience, vol. 26, No. 41, Oct. 11, 2006, 5 pages.
Courtine, G. et al., "Can experiments in nonhuman primates expedite the translation of treatments for spinal cord njury in humans?," Nature Medicine, vol. 13, No. 5, May 2007, 13 pages.
Drew, T. et al., "Cortical mechanisms involved in visuomotor coordination during precision walking," Brain Research Reviews, vol. 57, No. 1, Jan. 2008, Published Online Aug. 22, 2007, 13 pages.
Edgerton, V. et al., "Training Locomotor Networks," Brain Research Reviews, vol. 57, No. 1, Jan. 2008, Published Online Sep. 16, 2007, 25 pages.
Kwakkel, G. et al., "Effects of Robot-assisted therapy on upper limb recovery after stroke: A Systematic Review," Neruorehabilitation and Neural Repair, vol. 22, No. 2, Mar. 2008, Published Online Sep. 17, 2007, 17 pages.
Courtine, G. et al., "Recovery of supraspinal control of stepping via indirect propriospinal relay connections after spinal cord injury," Nature Medicine, vol. 14, No. 1, Jan. 6, 2008, 6 pages.
Cowley, K. et al., "Propriospinal neurons are sufficient for bulbospinal transmission of the locomotor command signal in the neonatal rat spinal cord," The Journal of Physiology, vol. 586, No. 6, Mar. 15, 2008, Published Online Jan. 31, 2008, 13 pages.
Vallery, H. et al., "Compliant Actuation of Rehabilitation Robots," IEEE Robotics & Automation Magazine, vol. 15, No. 3, Sep. 12, 2008, 10 pages.
Edgerton, V. et al., "Robotic Training and Spinal Cord Plasticity," Brain Research Bulletin, vol. 78, No. 1, Jan. 15, 2009, Published Online Nov. 14, 2008, 19 pages.
Fuentes, R. et al., "Spinal Cord Stimulation Restores Locomotion in Animal Models of Parkinson's Disease," Science, vol. 323, No. 5921, Mar. 20, 2009, 14 pages.
Alto, L. et al., "Chemotropic Guidance Facilitates Axonal Regeneration and Synapse Formation after Spinal Cord Injury," Nature Neuroscience, vol. 12, No. 9, Sep. 2009, Published Online Aug. 2, 2009, 22 pages.
Hagglund, M. et al., "Activation of groups of excitatory neurons in the mammalian spinal cord or hindbrain evokes locomotion," Nature Neuroscience, vol. 13, No. 2, Feb. 2010, Published Online Jan. 17, 2010, 8 pages.
Wessels, M. et al., "Body Weight-Supported Gait Training for Restoration of Walking in People With an Incomplete Spinal Cord Injury: A Systematic Review," Journal of Rehabilitation Medicine, vol. 42, No. 6, Jun. 2010, 7 pages.
Zorner, B. et al., "Profiling locomotor recovery: comprehensive quantification of impairments after CNS damage in rodents," Nature Methods, vol. 7, No. 9, Sep. 2010, Published Online Aug. 15, 2010, 11 pages.
Ada, L. et al., "Mechanically assisted walking with body weight support results in more independent walking than assisted overground walking in non-ambulatory patients early after stroke: a systematic review," Journal of Physiotherapy, vol. 56, No. 3, Sep. 2010, 9 pages.
Duschau-Wicke, A. et al., "Patient-cooperative control increases active participation of individuals with SCI during robot-aided gait training," Journal of NeuroEngineering and Rehabilitation, vol. 7, No. 43, Sep. 10, 2010, 13 pages.
Rosenzweig, E. et al., "Extensive Spontaneous Plasticity of Corticospinal Projections After Primate Spinal Cord Injury," Nature Neuroscience, vol. 13, No. 12, Dec. 2010, Published Online Nov. 14, 2010, 19 pages.
Hidler, J. et al., "ZeroG: Overground gait and balance training system," Journal of Rehabilitation Research & Development, vol. 48, No. 4, Available as Early as Jan. 1, 2011, 12 pages.
Musselman, K. et al., "Spinal Cord Injury Functional Ambulation Profile: A New Measure of Walking Ability," Neurorehabilitation and Neural Repair, vol. 25, No. 3, Mar. 2011, Published Online Feb. 25, 2011, 9 pages.
Harkema, S. et al., "Effect of Epidural stimulation of the lumbosacral spinal cord on voluntary movement, standing, and assisted stepping after motor complete paraplegia: a case study," The Lancet, vol. 377, No. 9781, Jun. 4, 2011, published Online May 20, 2011, 17 pages.
Wirz, M. et al., "Effectiveness of automated locomotor training in patients with acute incomplete spinal cord injury: A randomized controlled multicenter trial," BMC Neurology, vol. 11, No. 60, May 27, 2011, 5 pages.
Musienko, P. et al., "Controlling specific locomotor behaviors through multidimensional monoaminergic modulation of spinal circuitries," The Journal of Neuroscience, vol. 31, No. 25, Jun. 22, 2011, 32 pages.
Musienko, P. et al. "Multi-system neurorehabilitative strategies to restore motor functions following severe spinal cord injury," Experimental Neurology, vol. 235, No. 1, May 2012, Published Online Sep. 7, 2011, 10 pages.
Sun, F. et al., "Sustained axon regeneration induced by co-deletion of PTEN and SOCS3," Nature, vol. 480, No. 7377, Dec. 15, 2011, Published Online Nov. 6, 2011, 12 pages.

\* cited by examiner

PDMS-BASED STRETCHABLE MULTI-ELECTRODE AND CHEMOTRODE ARRAY FOR EPIDURAL AND SUBDURAL NEURONAL RECORDING, ELECTRICAL STIMULATION AND DRUG DELIVERY

TECHNICAL FIELD

The present invention relates to a device that is suitable for the electrical and/or pharmaceutical stimulation of the central nervous system, especially the spinal cord, or for recording neuronal signals, and to related methods of its use and manufacture.

PRIOR ART

Since Galvani's experiment on frog legs in the late 1780s, electrical stimulation of tissue or cells has been widely used by physiologists to investigate and understand the electrical properties of living organs and organisms. As a result, the first cardiac pacemaker was implanted in 1958 and now, more than 50 years later, pacemakers are improving the life of 600,000 patients every year. During the 1970s Michelson convinced the scientific community that meaningful sound could be transmitted to the brain by electrical stimulation of the cochlear nerve. Since then, over 200,000 people have received a cochlear implant and are able to understand human speech. Thanks to recent advances in neuroscience, deep brain stimulators are implanted to treat patients with tremor, Parkinson disease and epilepsy. Neurorehabilitation techniques are emerging such as cortical stimulation for treating stroke-related disorders, neurorobotic systems to replace impaired limbs, or retinal implants to restore vision. This was made possible by recent progresses in micro fabrication and electrode/cell interfaces.

Most of the known neuroprosthetic devices use a technology where metallic electrodes are microfabricated onto a biocompatible substrate of polyimide or parylene. Such devices show good flexibility and can be bent to conform to the environment which is favorable for the implantation and induce little inflammation to the surrounding tissue. However, they remain too stiff to be used in contact with moving tissues like muscles or the spinal cord, resulting in tissue damage, implant destruction or loose contacts between electrodes and targeted tissues.

Traumatic injuries of the spinal cord have long-term health, economic and social consequences, giving a sense of the urgency to the development of ways to treat them. Worldwide, an estimated 2.5 million people live with a chronic spinal cord injury (SCI). Individuals who remain permanently paralyzed after a SCI represent 50% of the total human disabled population. Consequently, there is a critical need to improve rehabilitative strategies to help these patients to regain the ability to stand or step.

Recently the impressive capacity of pharmacological and electrical spinal cord stimulations to promote full weight bearing walking in paralyzed rats when combined with rehabilitation was demonstrated in the paper [Courtine et al., "Transformation of nonfunctional spinal circuits into functional states after the loss of brain input", Nature Neuroscience 12, 10 (2009), pages 1333-U167]. Specifically, it was shown that epidural electrical stimulation (EES) applied at S1, L4, or L2 spinal segments could each promote unique patterns of locomotion, which were biased toward flexion when stimulating upper lumbar segments and toward extension when stimulating the sacral level.

In the paper [P. Musienko, R. van den Brand, O. Maerzendorfer, A. Larmagnac, and G. Courtine, "Combinatory electrical and pharmacological neuroprosthetic interfaces to regain motor function after spinal cord injury", IEEE transactions on Biomedical Engineering, Vol. 56, No. 11, November 2009], it was revealed that the combination of two, and even more efficiently three, sites of EES promoted clear synergistic facilitation of stepping in paralyzed rats. The paper presents a conceptual perspective on the use of neuroprosthetic devices to stimulate multiple spinal cord sites electrically and chemically. No information is provided regarding the procedures that could be employed to design the multi-electrode arrays (MEAs) necessary for such stimulation.

Such multi-electrode arrays should meet the following requirements: i) stable implantation over the dura for extended periods of time, ii) high flexibility, i.e. act as a second skin that bends with the spinal cord, iii) impermeability to body fluids to prevent short-circuits due to water absorption, iv) biocompatibility, v) capacity to deliver sufficient electrical charges to recruit neural structures while avoiding tissue damage, and vi) high spatial selectivity without overlapping stimulating fields.

U.S. Pat. No. 7,146,221 discloses a flexible electrode array for artificial vision. Gold electrodes and conductive leads are embedded in a stretchable PDMS substrate. The implant can be stretched to max. 3% without losing conductivity. This very limited amount of stretchability is due to the gold conductive leads that break easily and is insufficient for applications on the spinal cord.

The paper [Lacour, S. P., Wagner, S., Huang, Z. & Suo, Z., "Stretchable gold conductors on elastomeric substrates", Applied Physics Letters 82, 2404 (2003)] discloses a process for patterning gold thin films on PDMS. This process can produce gold structures that can resist 20% strain. However the measured impedance of such electrodes is too high for stimulation, and delamination of the gold electrodes will probably occur while applying too high voltages.

The paper [D. S. Pellinen, T. Moon, R. J. Vetter, R. Miriani, and D. R. Kipke, "Multifunctional flexible parylene-based intracortical microelectrodes", Proceedings of the 2005 IEEE Engineering in Medicine and Biology $27^{th}$ Annual Conference, Shanghai, China, Sep. 1-4, 2005, pages 5272-5275] describes flexible microelectrodes with integrated drug delivery channels. This implant can record neural activity and inject drugs locally. The substrate material used is parylene, which exhibits very limited flexibility and stretchability; as a consequence this implant is not stretchable and not suitable for use on the spinal cord.

The paper [F. Axisa, D. Brosteaux, E. De Leersnyder, F. Bossuyt, M. Gonzalez, M. Vanden Bulcke, and J. Vanfleeteren, "Elastic and Conformable Electronic Circuits and Assemblies using MID in polymer", Proceedings of the IEEE Polytronic 2007 Conference, pages 280-286] discloses the use of conductive polymers (silver filled silicone) on top of meander-shaped conventional gold tracks, so as to provide metallic stretchable conductors with high reliability. If a metallic conductor breaks, the conductive polymer acts like a bridge or shunt to ensure connectivity. This is demonstrated by a simple thermometer that can be stretched to 60%. No multi-electrode arrays for implantation are disclosed.

SUMMARY OF THE INVENTION

In a first aspect, it is an object of the present invention to provide a device for the electrical and/or pharmaceutical stimulation of the central nervous system or for recording neuronal signals, which is suitable to be implanted in an animal or human and may in particular be employed in the epidural or subdural space of the spinal cord.

The present invention thus provides a device for the electrical and/or pharmaceutical stimulation of the central nervous system, especially the spinal cord, or for recording neuronal signals, comprising:
  a conformable substrate which is primarily composed of (essentially consists of) a flexible and stretchable polymer; and
  a plurality of flexible electrodes and/or conductive leads embedded in the conformable substrate.

According to the present invention, the electrodes and/or leads are stretchable.

The present invention thus provides an implant comprising a polymer substrate of a compliant material, such as poly(dimethylsiloxane) or PDMS. The polymer substrate is conformable to the shape of the spinal cord. Stretchable electrodes and conductive leads which preferably are made of conductive PDMS are embedded in the polymer substrate. The conductive leads and electrodes are able to transmit signals under high mechanical stress. Optionally gold or other metals may be deposited on the conductive PDMS. In addition, the implant may be able to deliver drugs. To this end, the device may optionally comprise microfluidic channels inside of the polymer substrate, which are defined as chemotrodes, and which may be used for delivering pharmaceutical agents or treatments.

Using such an implant, electrical and pharmaceutical stimulation may be applied epidurally or subdurally to the spinal cord. In particular, the implant may be positioned under the dura thus providing improved fixation, reduced migration over time, closer and optimized positioning with respect to targeted neuronal structures for stimulating specific elements and recording neural activity, as well as for allowing local pharmaceutical stimulation.

Preferably the electrodes and/or leads are stretchable by at least 50% without losing their functionality, in particular, their electrical conductivity. The conducting and stretchable electrodes and/or leads are preferably essentially made of a polymer matrix with an embedded electrically conductive filler material. The filler material may be one of more of the following group: Ag, Au, Cu, Pt, Ir, Al, Fe, Cr, Ni, C, In, C, Sn, and Ti. The filler material may be present, e.g., in fibrous or particle or nanotube form. In alternative embodiments, the conducting and stretchable electrodes and/or leads may be essentially made of a conductive polymer (including polymers that are intrinsically conducting).

The device may further comprise fluidic channels that are embedded in the conformable substrate. In addition or in the alternative, the electrodes and/or leads may comprise a hollow channel susceptible of transporting a fluid. These channels may be used to supply a pharmaceutical to the implantation site.

The device may be provided with a reception means for contactless energy supply, preferably an electromagnetic coupling means. Such reception means are well known in the art and are widely employed, e.g., with cochlear implants. The device may further comprise an electrical circuit embedded into the flexible substrate or separately attached to the device. The electrical circuit may, e.g., be a circuit to control energy reception from an external energy source and/or to provide electrical stimulation signals to the electrodes of the device. The device may also comprise a battery, preferably a chargeable battery. In the case of a chargeable battery, the device preferably comprises reception means for receiving energy from an external energy supply in a contactless fashion, as already mentioned above, and an electrical circuit for charging the rechargeable battery with the received energy.

For implantation of the device on the spinal cord, it is preferred if the device has a total thickness of less than 1 mm, preferably less than 300 micrometers and most preferably less than 50 micrometers.

At least one of the electrodes and/or conductive leads may optionally be functionalized with a drug-releasing coating. The coating may, e.g., comprise polymer embedded vesicles to release small molecules (e.g. neurotransmitters) under electrical control, as described in [Norma Graf, Francesco Albertini, Tristan Petit, Erik Reimhult, Janos Vörös, Tomaso Zambelli, "Electrochemically Stimulated Release from Liposomes Embedded in a Polyelectrolyte Multilayer", Advanced Functional Materials (2011), DOI: 10.1002/adfm.201002283]. A drug-releasing coating may also be used to improve neural attachment and or to prevent unwanted immune reactions, e.g. fibrous tissue formation around the electrodes.

In a second aspect, the present invention provides a process for the manufacture of an implantable device for the electrical and/or pharmaceutical stimulation of the central nervous system or for recording neuronal signals. The process comprises:
  (a) forming a first layer of a non-conducting first conformable material;
  (b) applying structures of an electrically conducting second conformable material to the first layer of conformable material to form electrodes and/or leads;
  (c) applying a second layer of the first conformable material to the first layer and to the structures of second conformable material.

Before step (a), a carrier, which may optionally be covered with an anti-adhesion layer such as a polyimide or gold layer, may be provided. The first layer of the non-conducting first conformable material may then be formed by applying a precursor of the first conformable material to the carrier and curing the precursor to obtain the first conformable material. It is preferred that also the subsequent steps (b) and (c) are carried out while the first layer remains on the carrier, and that the carrier is removed from the first layer only after application of the second layer of the first conformable material.

The process may further comprise, after step (b), a step of depositing at least one metallic layer onto the second conformable material structures, in particular, a layer of silver or gold or platinum or iridium or any alloy of these materials. Prior to the deposition of the metallic layer, a layer of titanium may be deposited first to enhance the adhesion of the metallic layer on the second conformable material structures.

The process may further comprise, after step (b) and before or after step (c), a step of applying at least one contact layer on at least portions of the structures of the second conformable material to form electrodes and/or contact pads, the contact layer consisting of a conductive material different from the second conformable material. Examples include a conductive adhesive such as silver epoxy, a metal coating applied, e.g., by sputtering techniques, such as a Ti/Pt—Ir coating, or a metal foil such as Pt foil.

The process may comprise at least one step of injection molding and/or at least one step of screen printing or stamping and/or at least one step of photolithography.

According to another aspect of the present invention, electrical stimulation may be applied epidurally or subdurally to defined regions of the spinal cord utilizing an implant as defined above. Preferably, the device is implanted subdurally. In other words, the invention provides a method of neurostimulation, comprising:

implanting a device as defined above in the epidural or subdural space of the spinal cord of an animal or human; and
stimulating neurons in the spinal cord by providing electrical signals to the electrodes of the device.

According to yet another aspect of the present invention, pharmaceutical agents may be delivered to the epidural or subdural space using an implant as defined above. In particular, the invention further provides a method of drug delivery, comprising:

implanting a device as defined above in the epidural or subdural space of the spinal cord of an animal or human; and
delivering drugs to the epidural or subdural space through microfluidic channels embedded within the device.

Alternatively or additionally, pharmaceuticals may also be delivered to the epidural or subdural space using an implant as defined above, which has a drug-releasing coating.

According to yet another aspect of the present invention, neuronal signals may be recorded in the epidural or subdural space using an implant as defined above. In particular, the invention further provides a method of recording neural signals, comprising:

implanting a device as defined above in the epidural or subdural space of the spinal cord of an animal or human; and
recording neural signals received by the electrodes of the device.

In summary, the present invention suggests two independent, but related approaches to improve neural stimulation or recording at the spinal cord:

(1) The use of conductive PDMS as a stretchable and conductive material for creating conductive leads of a micro electrode array (MEA) for recording and stimulating neural tissue. This allows the MEA to be stretched beyond 50% and maintain good conductivity.
(2) The positioning of the array subdurally. This allows a markedly improved fixation of the array that reduces the risk of migration over time. The close and accurate positioning of the electrodes close to targeted neuronal structures enable delivery of more specific stimulations and improved recordings of neural activity.

In the prior art, MEAs have been successfully designed and manufactured for regions of the body that show limited motion, such as the brain, the retina, the cochlea etc. Instead, other regions such as the spinal cord move extensively during natural movement. As a result conventional MEAs can be severely damaged or damage the surrounding tissue. The present invention provides the design of a MEA that can conform to the spinal cord and move with it as opposed to against it. This is achieved by using a softer substrate like PDMS. PDMS has a much lower elastic modulus than conventionally patterned metallic leads. These leads usually break when the PDMS substrate is stretched to above 3%. It was shown that serpentine tracks can resist up to 10% strain. For higher strains other techniques are required. Carbon nanotubes gel, graphene, gold ion implantation, silver filled silicone, or liquid metal have been used in the prior art to make stretchable interconnects or electronics in other contexts. None of these techniques has been used for the design of stretchable implantable MEAs.

Concerning the second aspect, electrical stimulations have so far been delivered epidurally to alleviate pain or facilitate locomotion after spinal cord injury or Parkinson Disease. The specificity of spinal cord stimulation is limited by the relative large distance between the electrodes and the neural elements. Along the same line, neural activity has been recorded from the epidural space, but the obtained signals showed poor specificity, again due to the large distance between the electrode and the source of the neural signal. The present invention proposes to locate the electrodes closer to and more accurately from the targeted neural structures. This is achieved by positioning the electrodes subdurally to reduce the distance between the electrodes and the targeted neural elements.

The manufacture of a thin MEA allows the stable positioning of the electrodes close to spinal circuits and pathways while limiting the mechanical stress imposed on neural structures. In order to maintain fluid circulation and thermoregulation, small holes may be perforated throughout the MEA. The location of the MEA subdurally allows the delivery of drugs through chemotrodes defined as microfluidic channels embedded within the MEA. None of these techniques has been used in the prior art to stimulate the spinal cord electrically or pharmacologically.

In preferred embodiments of the present invention, conductive PDMS leads covered with gold or other metals are used; this solution demonstrates good stretchability and good conductivity. Other advantages are that it uses exclusively FDA-approved materials (silver, gold and PDMS) and that the contact pads are solderable to medical cable because of the deposited layer of gold. Another advantage of this solution is that the MEA is soft and thin enough to be implanted subdurally without damaging soft surrounding tissues; MEAs with stiffer substrate cannot be implanted there. Another advantage of the subdural location is the capability to deliver more specific electrical stimulations, to obtain improved neural recordings, and to deliver drugs through dedicated chemotrodes at specific segmental locations.

In general, the device according to the invention should make a tight connection to the tissue containing the cells of the central nervous system. To this end, the device may be provided with a plurality of holes or other surface topographies. These features serve to improve fluid circulation and thermoregulation when the device is implanted subdurally, and enable tissue to grow in through the holes or modulate tissue response by the corresponding topography.

The energy for the device can be delivered by contactless means, e.g. using electromagnetic coupling, light, heat or mechanical means, especially when the device according to the invention is embodied in a fully implantable form. When this is done, the electrodes can be controlled by an electric circuit that is embedded into the substrate or separately attached to the device. Means to achieve contactless energy transmission are well-known in the art and widely utilized, e.g. with cardiac pacemakers or cochlear implants. The electrodes can, however, also be attached to an outside power supply, for instance by means of surgical wires. For this, the device may comprise connecting pads to the electrodes. Another way of applying the electric signals is by aligning the electrodes or connecting pads with connecting pads of a second electronic device, meant as power supply and/or control, and by applying a conductive glue or epoxy, magnetic or mechanical coupling to form the electric connection between the two devices.

The fluidic channels or hollow electrodes of the device according to the invention can be used for delivering drugs, such as dopamine, serotonin or others. For this, a connection of some of the fluidic channels to the outside can be provided, if the device is fully implanted. Additionally or alternatively, the channels can be attached to a fluidic pump or some other drug delivery device. However, the fluidic channels or hollow electrodes can also be used to remove locally generated heat or unfavorable electrochemical products or waste products, or even to deliver surgical adhesives for fixation purposes.

The electrodes and/or leads can be arranged in a multitude of layers or any other three-dimensional geometry.

As material for the conductive material within the electrodes, Ag, Au, Cu, Pt, Ir, Al, Fe, Cr, Ni, C, In, C, Sn, Ti in fibrous or particle or nanotube form could be possible and can be embedded in a polymer matrix. Alternatively, a conductive polymer such as poly(pyrrole) or poly(aniline) can be used. It would also be possible to coat the conductive leads or electrodes with any of the aforementioned materials to achieve the conductivity.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

General Remarks

Figure 1:
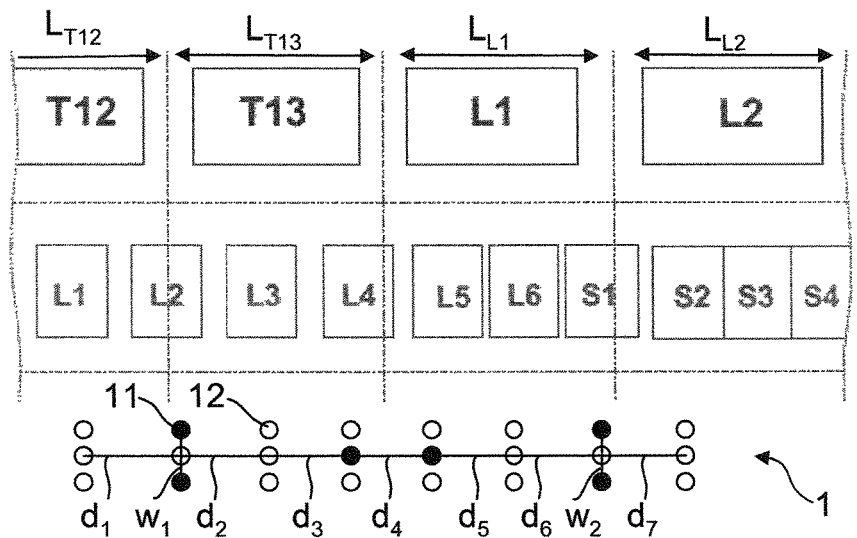
FIG. 1 illustrates the layout of a MEA having six electrodes, together with its intended position relative to the spinal cord.

In the following, preferred embodiments of PDMS-based stretchable microelectrode arrays (SMEA) for spinal cord stimulation are described. Such SMEAs were fabricated and tested in vivo on the spinal cord of rats. However, the invention is by no means limited to SMEAs suitable for implantation in rats or other rodents, and SMEAs of the type described in the following may also be employed with other vertebrates, including humans. Use of such SMEAs is not limited to implantation at the spinal cord. SMEAs of the type described here may also be employed in other body regions where they are subjected to strains.

The monolithic PDMS structure of the SMEA contained conductive PDMS (cPDMS) tracks, gold or platinum or platinum-iridium electrodes and contact pads connected to a head connector via medical fine wires. A PDMS substrate was used to reduce the mismatch between the mechanical properties of the implant and the spinal cord. The elastic and electrical properties of cPDMS promote high flexibility and stretchability to the implant, thus providing an electronic skin over the tissue. The SMEAs were implanted and tested chronically (2 months) in rats. Electrical epidural and subdural stimulation could induce spinal reflexes even at low current level (10 µA).

Polydimethylsiloxane (PDMS) was used as a substrate material because of its excellent biocompatibility and mechanical properties. Biological tissues like rat spinal dura mater were reported to have similar elastic modulus than PDMS (~1 MPa), whereas parylene and polyimide are 1000 times stiffer. This makes it challenging to produce conductive tracks that can stretch together with the PDMS substrate. It is assumed that strain greater than 20% can occur during chronic implantation in rats, while sputtered gold tracks on PDMS can generally only survive up to 1% strain. Conductive PDMS prepared by dispersing silver particles or carbon nanotubes in the PDMS matrix can remain conductive at strains >60%. In the preferred embodiments of the present invention, described in more detail below, cPDMS tracks were integrated into a PDMS structure to produce a monolithic PDMS-based MEA that remains conductive while being stretched above 30% or even above 50%.

Preparation of cPDMS

To prepare the conductive PDMS, silver particles were dispersed into a PDMS mixture until a smooth paste was obtained. 5 g of PDMS (Sylgard 184, Dow Corning) was prepared by mixing base and curing agent in a 10:1 (w/w) ratio. 12-14 g of silver powder (2-3 µm near-spherical particles) were progressively dispersed into the PDMS mixture by using a miller or sonication tip. Hexane was used to lower the viscosity of the preparation in order to facilitate the milling. The resulting smooth paste was degassed for 15 min in a desiccator. The cPDMS mixture could be kept over months in a freezer at −20° C.

Preparation of Copper Stencils

To prepare the stencils, prior to screen-printing the cPDMS electrodes, copper foils of 75 µm thickness were wet etched from both sides. Copper foils of dimension 76 mm×26 mm were rinsed in acetone, isopropanol, blow dried with a nitrogen gun, activated in Oxytron 15™ (Oxy Metal Industries) solution, rinsed in milliQ™ filtered and deionized water and again blow-dried. Positive photoresist 1805 was spin coated at 500 rpm for 30 s and cured at 85° C. for 10 min on both sides. The foils were precisely positioned and fixed between 2 masks, exposed to UV from one side for 45 s, returned and exposed for another 45 s. The photoresist was developed in Micropposit™ Developer for 3 s and rinsed in milliQ™ water. The copper substrate was etched from both sides in a copper etching solution until complete dissolution of the copper. The photoresist was then stripped in acetone. The copper stencils were rinsed in milliQ™ water and blow-dried.

Array Layout

Different layouts were used in this study. Array with six or eight electrodes were produced. The term electrode is to be understood in the usual manner to relate to an electrically conducting element that is exposed to the environment. FIG. 1 illustrates the layout for the six-electrode array. Six electrodes 11 are arranged on an imaginary array 12 with three rows and eight columns in the following positions (first number indicates row, second number indicates column): (1, 2), (3, 2), (2, 4), (2, 5), (1, 7), (3, 7). The rows and columns are not necessarily equidistant and not even necessarily parallel. In the present example, the distance between the first and second column is $d_1=3.0$ mm, while the distance between subsequent columns is $d_2=d_3=d_4=d_5=d_6=d_7=2.5$ mm. The distance between rows decreases in the present example from left to right, with a row-to-row center distance of $w_1=1.0$ mm at the position of the second column and $w_2=0.7$ mm at the position of the seventh column. In particular, the present layout and dimension are adapted to neurostimulation at the spinal cord of adult rats, in the position near vertebrae T12, T13, L1 and L2 and spinal segments L1-L6 and S1-S4, as shown in FIG. 1. Typical length dimensions of these vertebrae are $L_{T12}=6.8$ mm, $L_{T13}=7.2$ mm, $L_{L1}=7.5$ mm, and $L_{L2}=7.8$ mm. The electrodes of the array are arranged such that they span a plurality of spinal segments, here six such segments. Of course, other layouts and dimensions are conceivable, depending on the intended application. By the way of example, if the array is intended to be used with humans, the arrangement of electrodes will be adapted to the size of the human vertebrae and spinal segments accordingly so as to span a plurality of human spinal segments.

Figure 2:
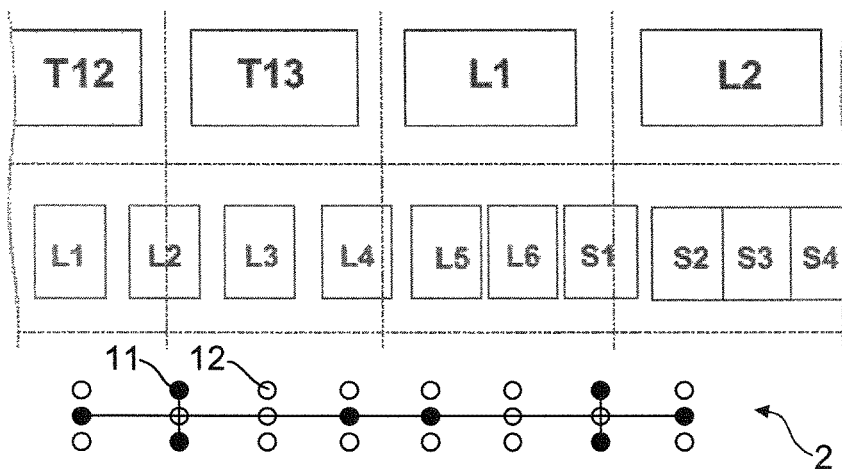
FIG. 2 illustrates the layout of a MEA having eight electrodes, together with its intended position relative to the spinal cord.

FIG. 2 illustrates a corresponding layout for an eight-electrode array. The layout corresponds to the layout of FIG. 1, with two additional electrodes at positions (2, 1) and (2, 8).

Fabrication of the SMEA

In the following, various processes that may be employed for the manufacture of SMEAs according to the present invention are described by the way of example.

In general terms, to prepare the SMEA, cPDMS structures were applied on a PDMS substrate by using custom-made copper stencils or screen-printed with commercially available screens. A second layer of PDMS was deposited as an insulation layer.

Figure 3:
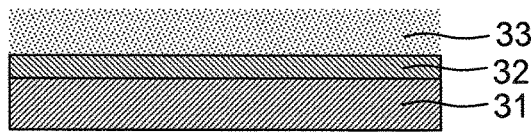
FIG. 3 illustrates the layer sequence for the preparation of a PDMS layer on a glass slide carrier.

100 μm thick Kapton foils of dimensions 76 mm×26 mm were deposited on microscopy glass slides with same dimensions. Adhesion was realized by adding a drop of water between the Kapton foil and the glass substrate. The Kapton foils were used as anti-adhesion layer for the PDMS. FIG. 3 schematically illustrates the resulting layer sequence after application of the first PDMS layer. A carrier 31 in the form of a microscopy slide carries an anti-adhesion layer 32 in the form of a Kapton foil, which in turn carries a first layer of a conformable substrate, here in the form of a PDMS layer 33. As an alternative to a polyimide layer such as a Kapton layer, a thin gold film, a Ti/Au film, a Teflon coating, a polymeric coating like PMMA or polyimide or a layer of alkoxysilane molecules may be deposited as an anti-adhesion layer 32 on the carrier 31 (here a glass slide).

A first layer (30-50 μm thick) of PDMS was spin coated at 3000 rpm for 30 s on the Kapton or gold layer and cured at 100° C. for 30 minutes on a hotplate. There are different curing protocols for PDMS: temperatures ranging from 25° C. up to 150° C. with curing times ranging from 10 minutes up to 2 days in an oven or on a hotplate can be used.

These initials steps are the same for the following different processes.

First Process

Figure 4:
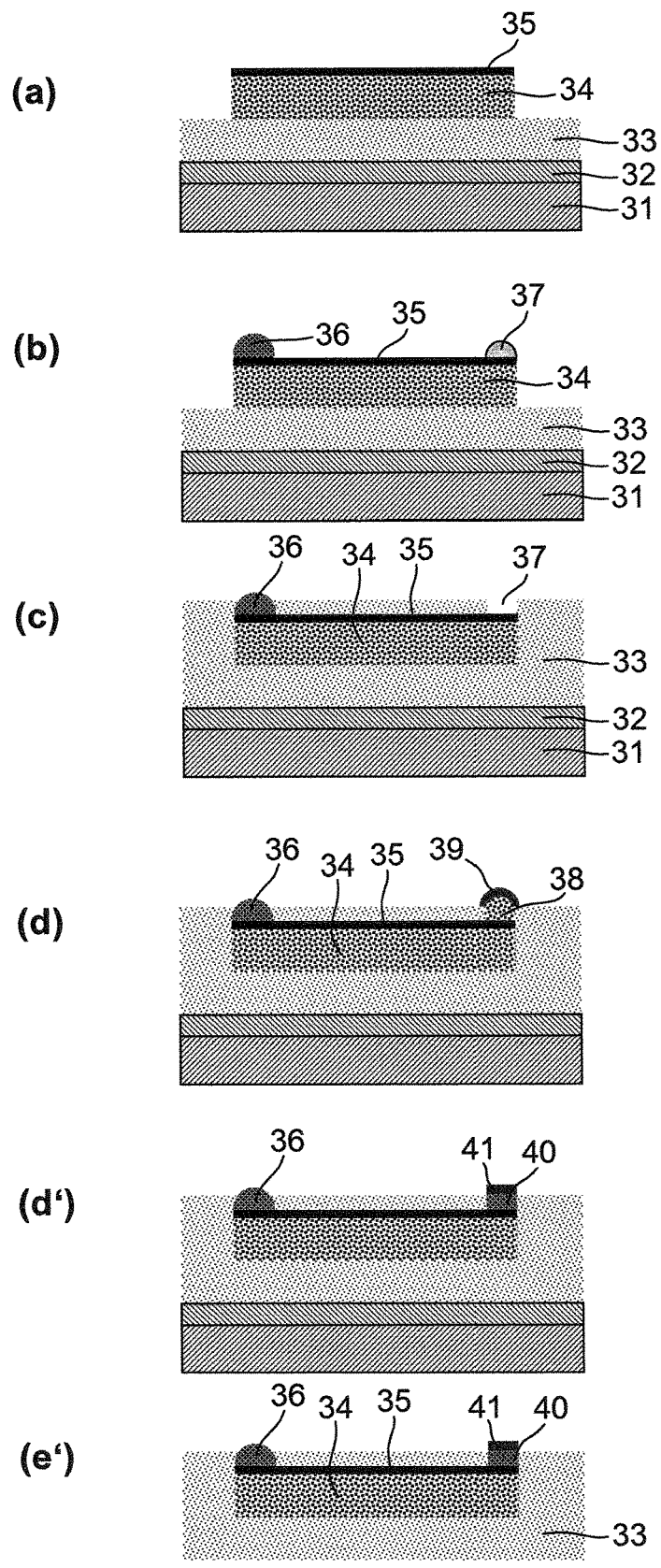
FIG. 4 illustrates a first preferred process for manufacturing a SMEA.

A first exemplary process is illustrated in FIG. 4. The copper stencils, as described above, were gently pressed against the PDMS substrate 33. cPDMS was spread with a blade over the stencils. The stencils were carefully peeled off, leaving cPDMS structures 34 on the PDMS substrate, cleaned in toluene, rinsed in isopropanol, milliQ™ water and blow-dried. As an alternative, commercially available screens with stainless steel mesh of 30 μm aperture and 40 μm thick photoresist are also suitable for this process. The screen is then positioned parallel to the substrate at a distance of 30 mm, and the structures are printed using standard techniques. The cPDMS structures were cured at 100° C. for 3 hours in an oven or on a hotplate. In an optional step, the stencils were put back on the PDMS substrates and used as shadow masks to sputter Ni and Ag layers of 15 nm and 100 nm thickness, respectively, on the cPDMS structures. The optional Ag layer 35 increases the conductivity of each track and promotes an adhesive substrate for making the contact pads (FIG. 4(a)). Gold or platinum may be used instead of silver for the layer 35. Drops of conductive silver epoxy 36 were manually deposited on each contact pad and cured at 130° C. for 1 hour in an oven. Drops of SU-8 negative photoresist 37 were manually deposited on each electrode and cured at 95° C. for 1 hour on a hotplate (FIG. 4(b)). A second layer of PDMS was spin coated at 1200-1400 rpm for 30 s to make an insulation layer. SU-8 bumps were mechanically removed (FIG. 4(c)) and the holes were either manually filled with cPDMS, and cured at 100° C. for 2 hours in an oven or on a hotplate in order to make bumpy electrodes 38, or manually filled with silver epoxy, and cured at 130° C. for 1 hour in an oven in order to make flat electrodes 40. Ti/Pt—Ir layers 39 or 41 of 15 nm/300 nm were sputtered on each electrode by using shadow masks similar to that previously described (FIG. 4(d) and FIG. 4(d'), respectively). The resulting SMEA was peeled off from the carrier 31 and anti-adhesion layer 32 (FIG. 4(e')).

Second Process

Figure 5:
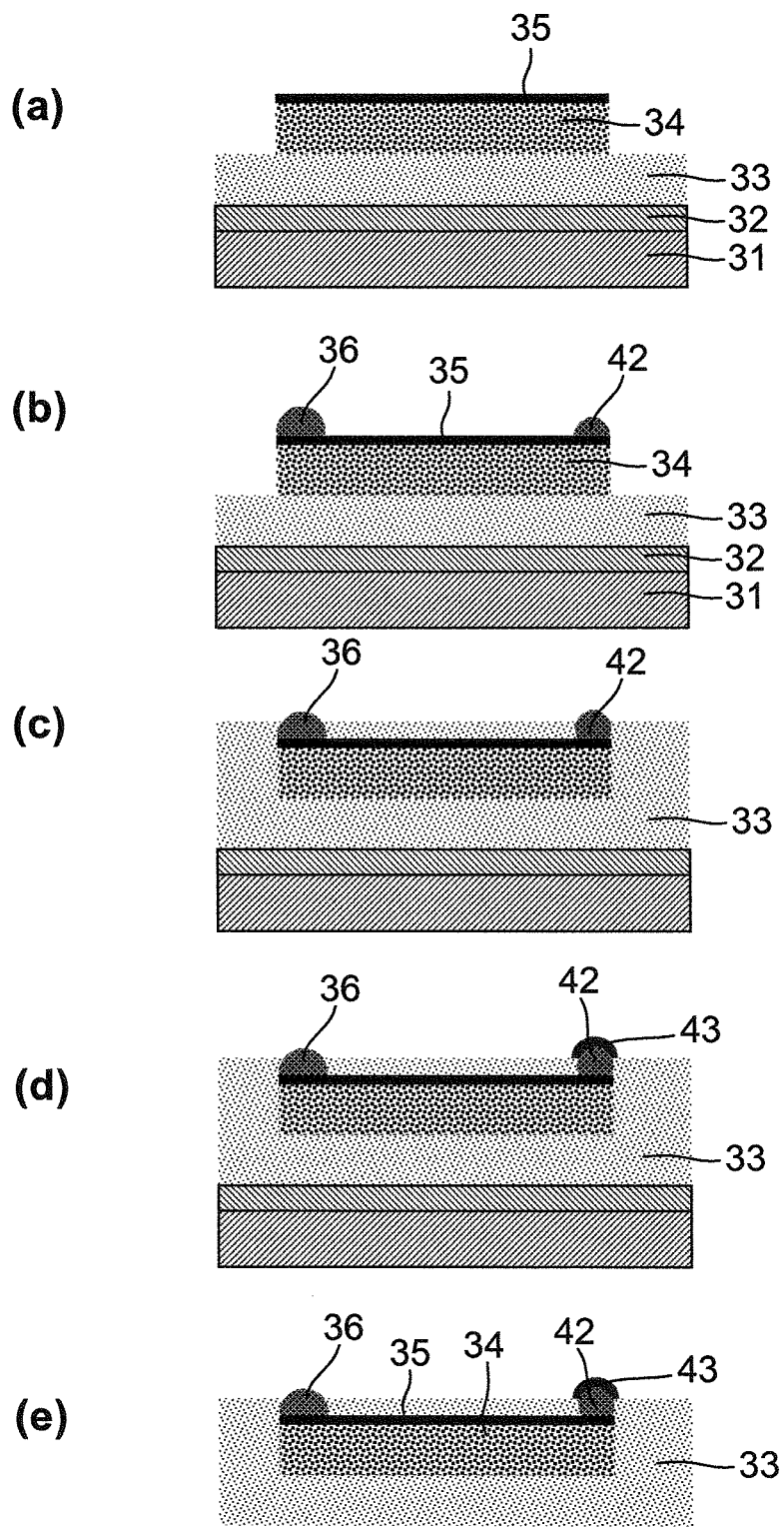
FIG. 5 illustrates a second preferred process for manufacturing a SMEA.

A second process is illustrated in FIG. 5. As in the first process, cPDMS structures 34 were obtained on the PDMS substrate 33 and cured at 100° C. for 3 hours in an oven or on the hotplate, and optionally Ni/Ag layers 35 of 15 nm/100 nm were sputtered onto the cPDMS structures 34 (FIG. 5(a)). Drops of conductive silver epoxy 36, 42 were manually deposited on each contact pad and electrode and cured at 130° C. for 1 hour in an oven (FIG. 5(b)). A second layer of PDMS was spin coated at 1200-1400 rpm for 30 s to make an insulation layer (FIG. 5(c)). The thin PDMS insulation layers over the electrodes were manually removed and Ti/Pt—Ir layers 43 of 15 nm/300 nm were sputtered on each electrode by using shadow masks similar to those previously described (FIG. 5(d)). Finally, the resulting SMEA was removed from the carrier 31 and anti-adhesion layer 32 (FIG. 5(e)).

Third Process

Figure 6:
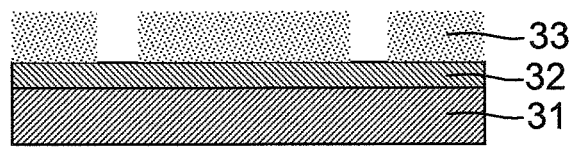
FIG. 6 illustrates a third preferred process for manufacturing a SMEA.
Figure 6:
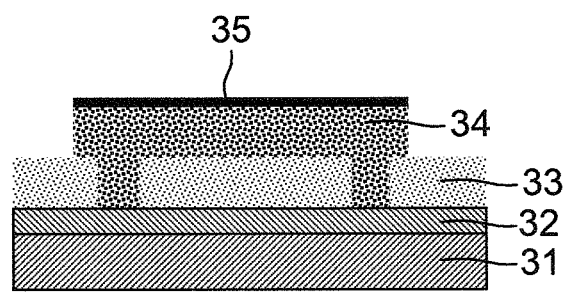
Figure 6:
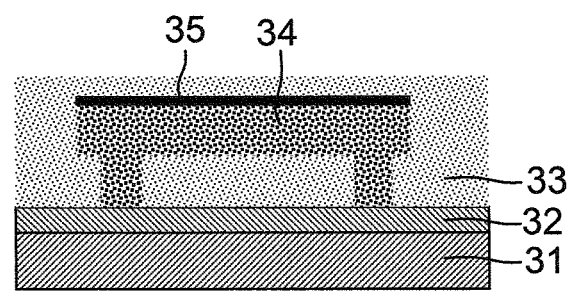
Figure 6:
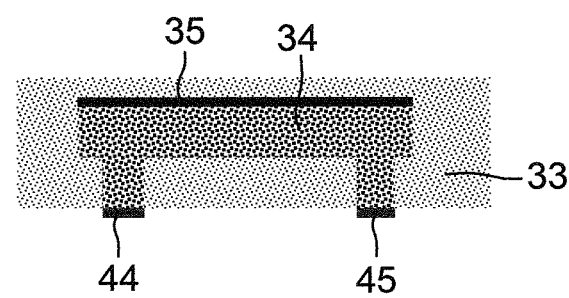

A third process is illustrated in FIG. 6. Holes of 350 μm were manually punched through the PDMS layer 33 at the location of the pads and electrodes (FIG. 6(a)). The copper stencils were then carefully positioned and gently pressed against the PDMS substrates 33. cPDMS was spread with a blade over the stencils. The stencils were carefully peeled off leaving the cPDMS structures 34 on the PDMS substrate, cleaned in toluene, rinsed in isopropanol, milliQ™ water and blow-dried. The cPDMS structures 34 were cured at 100° C. for 3 hours in an oven or on the hotplate. The stencils were put back on the PDMS substrates and used as shadow masks to sputter Ni/Ag layers 35 of 15 nm/100 nm on the cPDMS structures 34 (FIG. 6(b)). A second layer of PDMS was spin coated at 1200-1400 rpm for 30 s to make an insulation layer (FIG. 6(c)). The array was removed from the carrier 31, 32, flipped and put back onto the carrier. Ti/Pt—Ir layers 44, 45 of 15 nm/300 nm were sputtered on each electrode and pad by using shadow masks similar to those previously described (FIG. 6(d)).

Fourth Process

Figure 7:
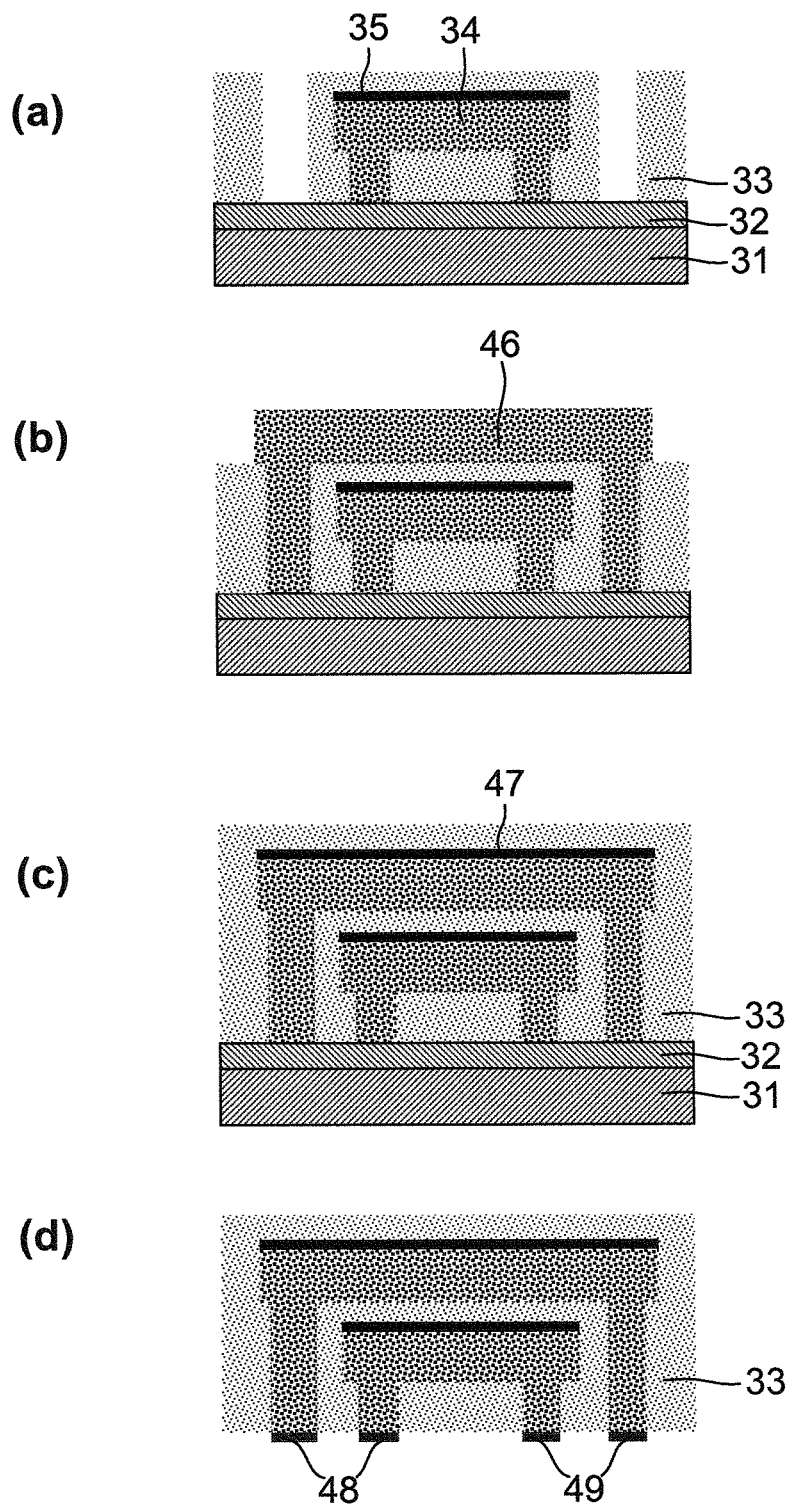
FIG. 7 illustrates a fourth preferred process for manufacturing a SMEA.

A fourth process is illustrated in FIG. 7. This process is used to produce 3D structures with twice more electrodes. A structure as shown in FIG. 6(c) was manufactured as described in conjunction with the third process. These steps were repeated once more in order to get structures (second cPDMS structure 46, second Ni/Ag layers 47) in two different planes with a doubled amount of electrodes (FIGS. 7(b) and (c)). The array was removed from the carrier 31, 32, flipped and put back onto the carrier. Ti/Pt—Ir layers 48, 49 of 15 nm/300 nm were sputtered on each electrode and pad by using shadow masks similar to those previously described (FIG. 7(d)).

Fifth Process

Figure 8:
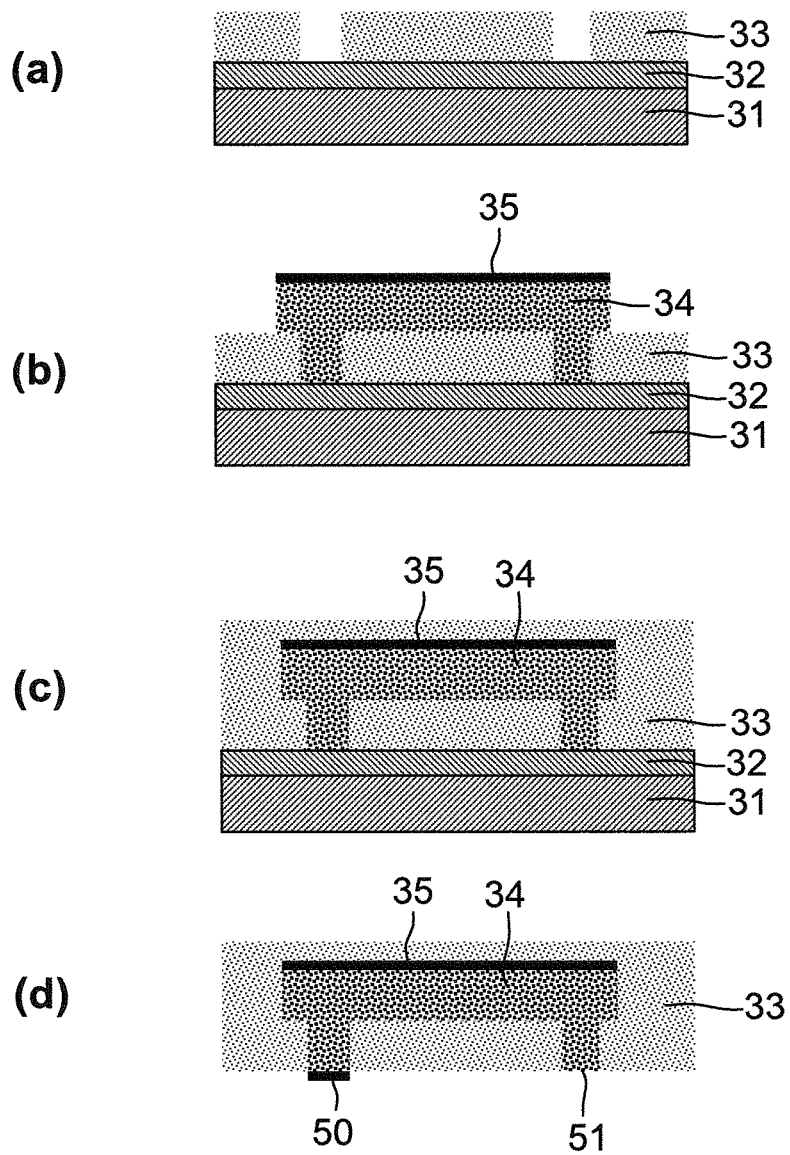
FIG. 8 illustrates a fifth preferred process for manufacturing a SMEA.

A fifth process is illustrated in FIG. 8. In this process, platinum is used as a filler to produce cPDMS. As a result, cPDMS can directly be used as an electrode material. Holes of 350 µm were manually punched through the PDMS layer 33 at the location of the pads and electrodes (FIG. 8a). The copper stencils were then carefully positioned and gently pressed against the PDMS substrates. cPDMS was spread with a blade over the stencils. The stencils were carefully peeled off leaving the cPDMS structures 34 on the PDMS substrate 33, cleaned in toluene, rinsed in isopropanol, milliQ™ water and blow-dried. The cPDMS structures 34 were cured at 100° C. for 3 hours in an oven or on the hotplate. The stencils were put back on the PDMS substrates and used as shadow masks to sputter Ni/Ag layers 35 of 15 nm/100 nm on the cPDMS structures (FIG. 8(b)). A second layer of PDMS was spin coated at 1200-1400 rpm for 30 s to make an insulation layer (FIG. 8(c)). The array was removed from the carrier 31, 32. The array does not need an extra electrode coating. Ni/Ag layers 50, 51 are sputtered on the pads to promote adhesion for silver epoxy (FIG. 8(d)).

Sixth Process

Figure 9:
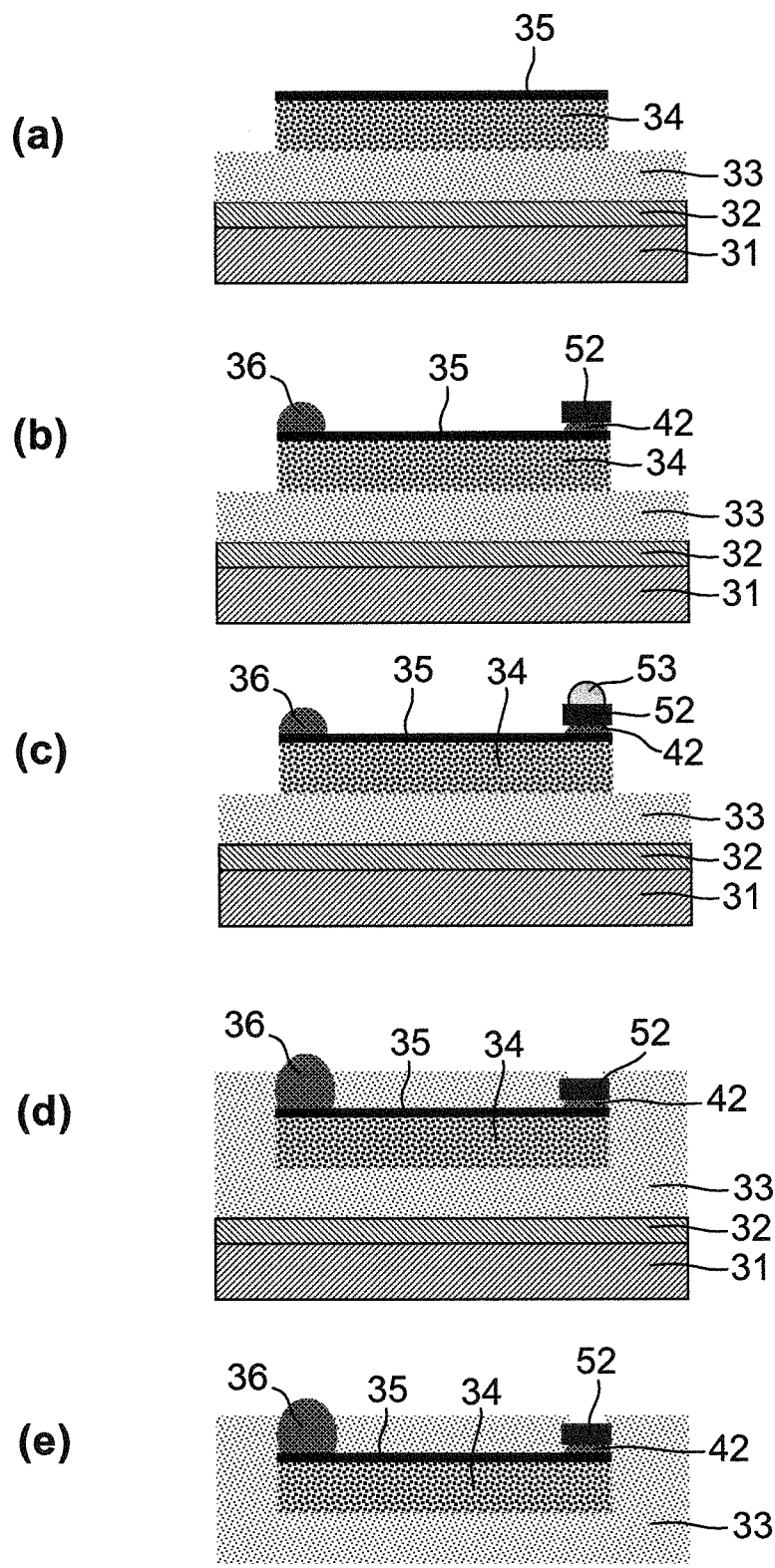
FIG. 9 illustrates a sixth preferred process for manufacturing a SMEA.

A sixth process is illustrated in FIG. 9. cPDMS structures 34 with Ni/Ag layers 35 were prepared as before (FIG. 9(a)). Drops of conductive silver epoxy 36, 42 were manually deposited on each contact pad and electrode and cured at 130° C. for 1 hour in an oven. Prior to curing, platinum disks 52 of 350 µm diameter, obtained from a 12.5 µm thick platinum foil were manually placed over each electrode (FIG. 9(b)). The adhesion and electrical contact between the cPDMS and Pt disks are provided by the silver epoxy. Drops of SU-8 photoresist 53 were manually deposited on each electrode and cured at 95° C. for 1 hour on a hotplate (FIG. 9(c)). A second layer of PDMS was spin coated at 1200-1400 rpm for 30 s to make an insulation layer. SU-8 bumps were mechanically removed to expose the Pt electrodes (FIG. 9(d)), and the SMEA was peeled off from the carrier 31, 32 (FIG. 9(e)).

Seventh Process

Figure 10:
FIG. 10 illustrates a seventh preferred process for manufacturing a SMEA.
Figure 10:
Figure 10:
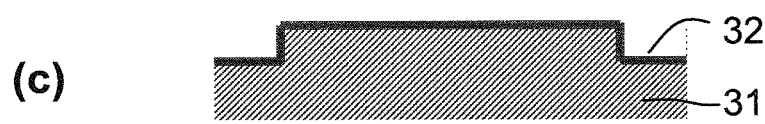
Figure 10:
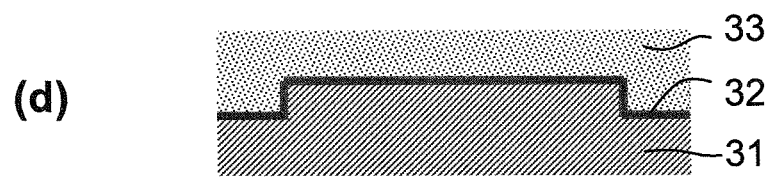
Figure 10:
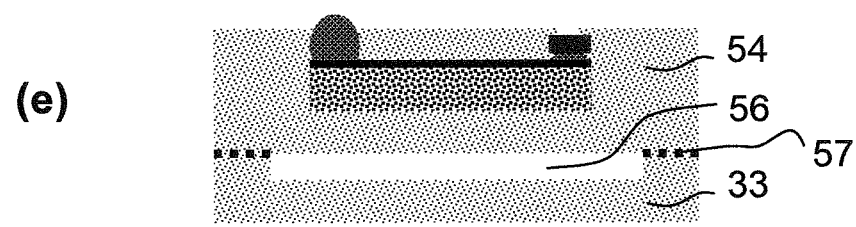
Figure 10:
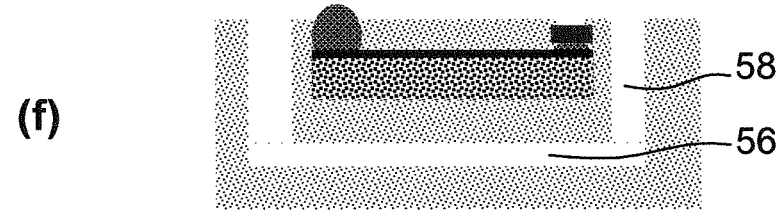

In the following, a process for preparing a SMEA containing fluidic channels (microchannels defining chemotrodes) is described by the way of example with reference to FIG. 10. PDMS is first casted on a structured carrier whose structures correspond to the geometry of the desired microchannels. The structured carrier 31 can be produced either by making structures of photoresist like SU8 on a carrier like glass or silicon using standard photolithography or by wet etching, dry etching or laser ablating the carrier (FIG. 10(a) and (b)). The structured carrier 31 is then coated with an anti-adhesive layer 32 that facilitates the later peeling of the PDMS layer (FIG. 10(c)). The anti-adhesive layer 32 can be a metallic layer e.g. Ti/Au, a Teflon coating, a polymeric coating like PMMA or polyimide or a layer of alkoxysilane molecules. PDMS is spin-coated on the structured substrate and then cured (FIG. 10(d)). The PDMS is then peeled off from the carrier. The obtained micro-structured PDMS layer is flipped and bonded on the back of a device 54, which may have been prepared according of one of the processes described before. The bonding of the two PDMS layers is made by first treating the surface to be bonded in air plasma, placing the layers against each other, pressing and waiting until the two layers are bonded (symbolized by connection 57). This results in horizontal channels 56 between the two layers. Holes 58 for liquid outlet and inlet are drilled with a laser.

Eighth Process

In an alternative process for preparing a SMEA with fluidic channels, a device fabricated, e.g., according to one of the processes described before is flipped and its bottom surface is micromachined with a laser. Holes and microchannels are drilled with a laser. Then a layer of PDMS is bonded as described before to close the microchannels.

Regardless of how the microchannels were produced, a small stainless steel cannula may be used to make the interconnection between a small tube of the pump and the inlet of the microchannels. The diameter of the cannula is bigger than that of the tube and inlet to avoid leakage. The interconnection is sealed in PDMS.

EXAMPLE

SMEA Produced by Sixth Process

Figure 11:
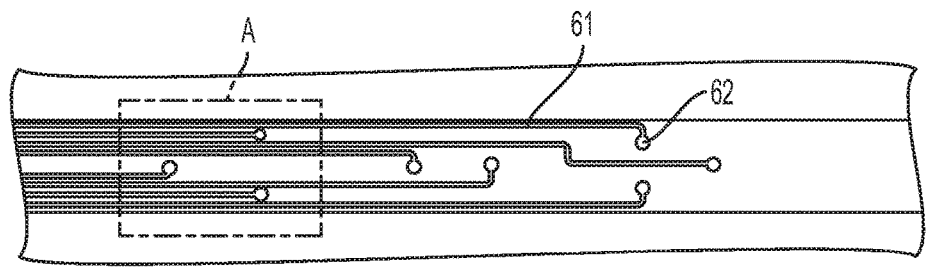
FIG. 11 shows part of a SMEA produced using the sixth process, carrying an array of eight platinum electrodes.
Figure 12:
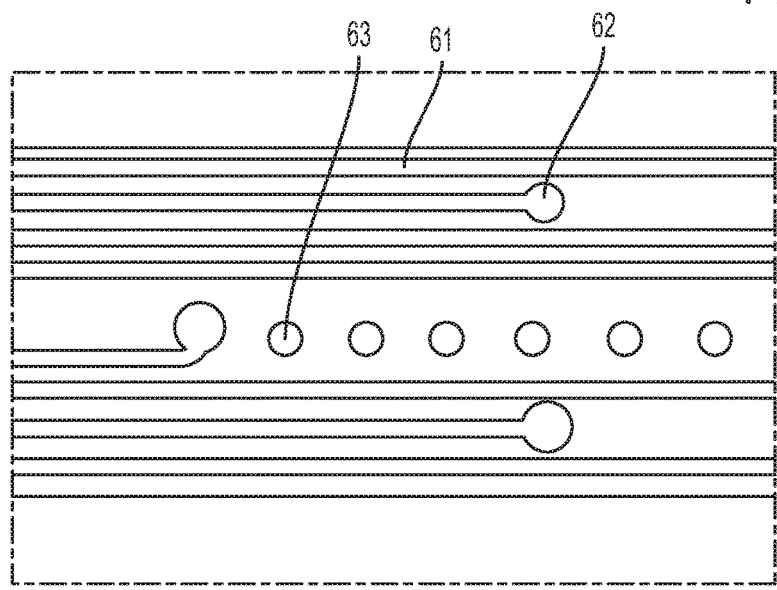
FIG. 12 shows detail (A) of FIG. 11 on an enlarged scale.

FIGS. 11 and 12 show an array of eight platinum electrodes 62 in the arrangement of FIG. 2, produced using the sixth process as shown in FIG. 9. The width of each conductive track 61 is 150 µm. The minimum distance between two next-neighbor tracks is 150 µm. The diameter of each electrode 62 is 350 µm. Holes 63 of 350 µm diameter are visible. The thickness of the array is within the range of 100-200 µm. It does not exceed 300 µm. The width of the array is within the range of 2.8-3.0 mm.

Figure 13:
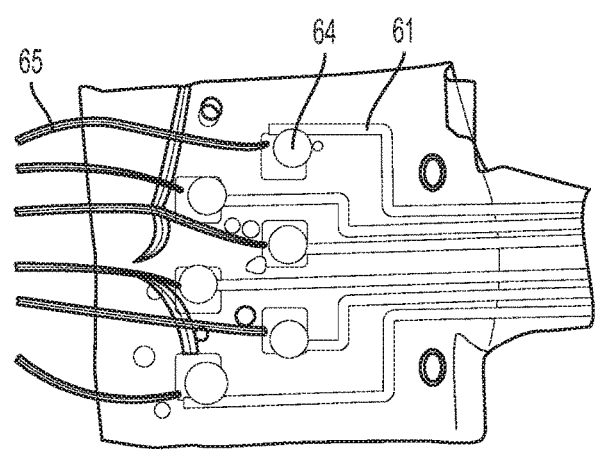
FIG. 13 illustrates the connection of the SMEA to a head connector.

Omnetics™ circular connectors were used as headplugs for the rats. Medical fine wires 65 with stainless steel core and PTFA insulation were used to connect the array to the headplug at the contact pads 64, as shown in FIG. 13. To this end, the insulation was removed from the tip of each fine wire 65. Each tip was then placed on top of a contact pad 63. Ag-epoxy was used to electrically connect wires and pads. The Ag-epoxy was cured for 1 hour at 130° C. in an oven. A PDMS layer was then casted on the region of the contact pads to cover the contact pads and the Ag-epoxy.

The electrical properties of the SMEA were measured with contact probes. Electrical resistivity of conductive tracks was measured with a multimeter between contact pads and respective electrodes. For Ag-coated tracks, the resistivity did not exceed 50Ω. For non Ag-coated tracks, the resistivity was in the range 100Ω-200Ω.

Figure 14:
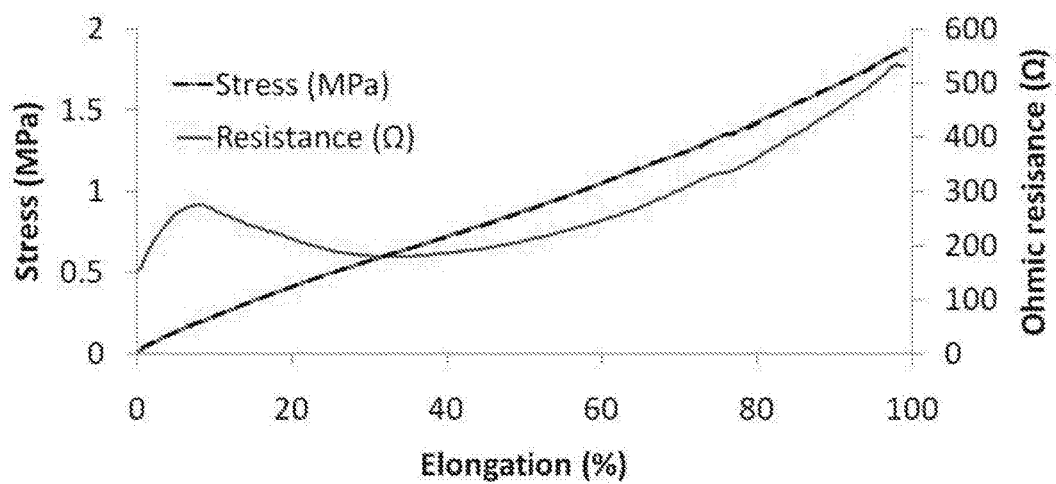
FIG. 14 shows a diagram in which stress and resistance are plotted over elongation of the SMEA of FIGS. 12 and 13.

A non Ag-coated track was stretched and its resistivity was measured with a multimeter as a function of elongation. The stretching speed was 0.1 mm/s. The results are shown in FIG. 14. Stress increased linearly with elongation, as expected. Resistivity first increased with elongation, then slowly dropped again to reach a local minimum at about 40% elongation, before slowly rising again. The resistivity changed by less than a factor of 3 for an elongation range of 0-100%.

Preliminary investigations of AC impedance showed that the impedance of the tested electrodes was in the range 2-50 kΩ at a frequency of 1 kHz.

Epidural and Subdural Implantation

Figure 15:
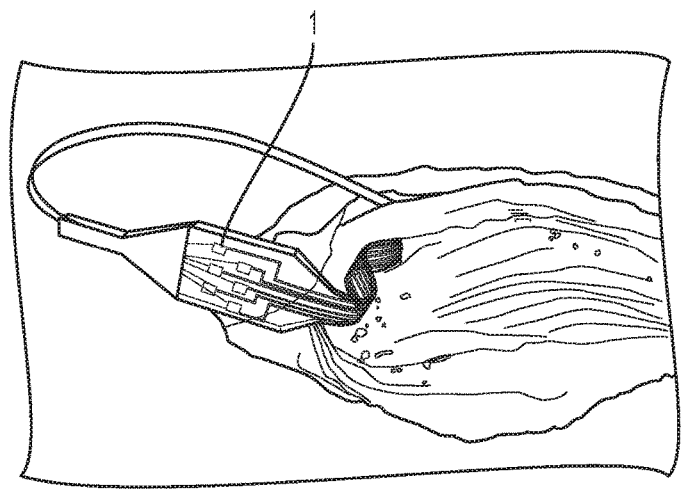
FIG. 15 shows implantation of a SMEA with six electrodes into a rat.
Figure 16:
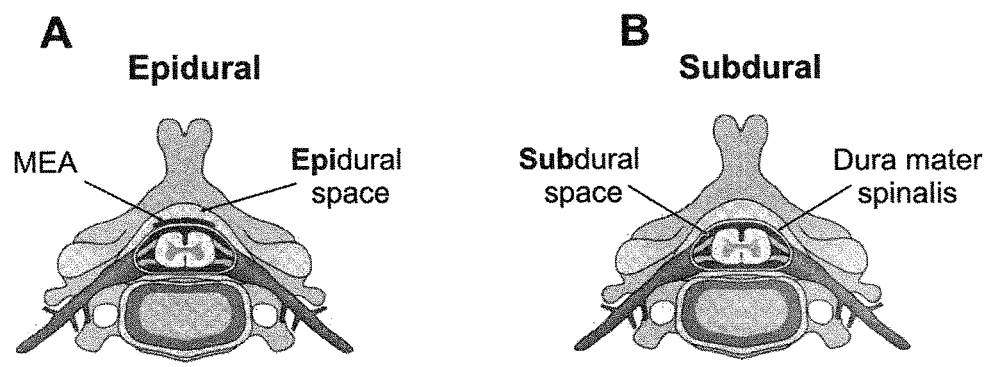
FIG. 16 illustrates implantation in the epidural space (part A) as compared to the subdural space (part B)

A SMEA 1 as described above was positioned on the spinal cord of a rat (FIG. 15) in the epidural or subdural space (FIG. 16). The advantages of epidural implantation are that epidural implantation is less invasive, technically simpler and less traumatic. However, the specificity of the epidural spinal cord stimulations is limited by the relative large distance between the electrodes and the neural elements. Neural activity has been recorded from the epidural space, but the obtained signals showed poor specificity due to the large distance between the electrode and the source of the neural signal. It is therefore desirable to position the electrodes closer to and more accurately from the targeted neural structures. This can be achieved by positioning the electrodes subdurally to reduce the distance between the electrode and the targeted neural elements. The presently proposed thin and flexible MEA allows the stable positioning of the electrodes close to spinal circuits and pathways while limiting the mechanical stress imposed on neural structures. In addition, the location of the MEA subdurally allows the delivery of drugs to cerebrospinal fluid through chemotrodes defined as microfluidic channels embedded within the MEA bypassing the blood-brain barrier.

Figure 17:
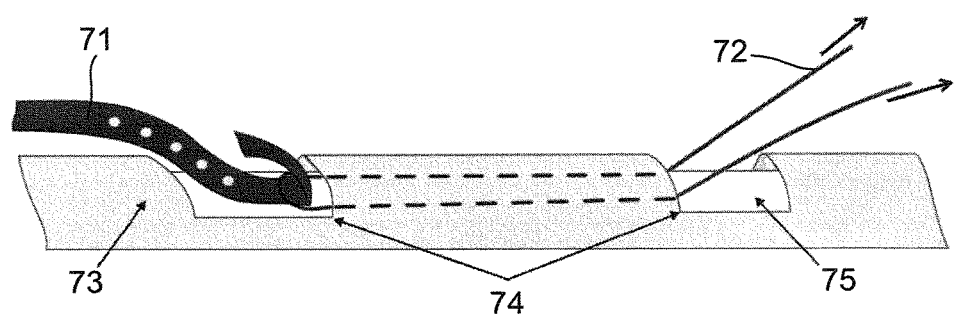
FIG. 17 illustrates a protocol for subdural implantation of a SMEA.
Figure 18:
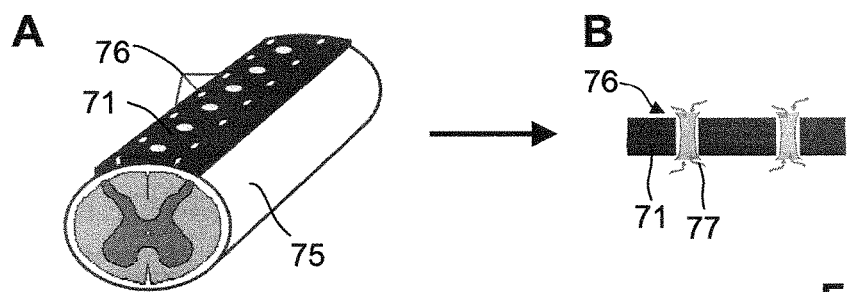
FIG. 18 illustrates improved fixation of the SMEA by multiple holes.

FIG. 17 illustrates an exemplary subdural implantation technique. To pass the electrode between the spinal cord 75 and vertebral column 73, rostral and caudal laminectomies 74 were made (i.e. incisions of dura mater spinalis were performed), exposing the spinal cord 75. Ethilon 4.0 suture 72 was used for guiding the SMEA 71 and pulling the SMEA into the subdural space between the spinal cord and the vertebral column. Multiple holes 76 were prepared in the SMEA 71 between the electrodes for fixation of the implant to the dura (FIG. 18(A)). Connective tissue 77 grows through the holes in 1-2 weeks after implantation and efficiently stabilizes the implant (FIG. 18(B)). In addition the holes maintained fluid circulation and thermo-regulation throughout the MEA.

The positioning of the array subdurally allowed a markedly improved fixation of the array by the dura mater, which reduces the risk of migration over time. The close and accurate positioning of the electrodes close to targeted neuronal structures enabled delivery of more specific stimulations and improved recordings of neural activity. A stress-release loop placed intramuscular before entrance of the MEA under the vertebrae additionally saved the stable position of the implant on the cord.

To improve biocompatibility the appropriate size, form and thickness of PDMS in MEA components (connector, release loop, electrode array) were chosen according to the different steps of the surgical procedure. Properties of the electrode array were further optimized on basis of feedback from in-vivo experiments, dissection and histological evaluation of the biological tissue around the implant. The materials did not adversely affect the integrity of tissue culture.

Preliminary testing in rats with chronically implanted MEA over lumbosacral segments showed no sign of inflammation and preserved implant integrity two weeks after surgery. As early as one week after a complete spinal cord transection, EES applied at the various electrodes of the MEA could encourage continuous locomotion on the treadmill. For testing this, the rats were positioned over a treadmill. Drugs were first injected. Then electrical stimulation was applied to each electrode and the minimal current amplitude for which response in the hind limbs' muscles was observed (using EMG recordings) was determined as well as the specific pattern of muscle activation. The electrical stimulus that was applied had the following parameters: Monopolar stimulation between one epidural electrode and a common counter electrode located in the back. Bipolar stimulation between two epidural electrodes. Current amplitude ranging from 10 μA up to 1 mA. Biphasic square pulse, cathodic first, 200 μs up to 1 ms for each phase. Frequency between 20 and 100 Hz.

The experiments showed that, by using single-site EES, paralyzed rats were able to walk. However the locomotion was not optimal meaning that there is a significant difference with a non-injured rat. In order to improve the locomotion of the paralyzed rats, multi-site EES was used. It had already been shown that simultaneous monopolar stimulations at two locations can improve the locomotion. By the help of the presently proposed SMEAs, it could be shown that it is possible to do even better by applying monopolar stimulations at different sites and at different moments. For example, after figuring out which electrode is responsible for the right leg flexion, electrical stimulation may be applied to that electrode only during the swing phase of the right limb. By doing so, the superiority of the new stimulation paradigm could be demonstrated, which is made possible by the presently proposed electrode arrays.

The invention claimed is:

1. An implantable device for electrical and pharmaceutical stimulation of a central nervous system which is configured and arranged for implantation in an animal or human in an epidural or subdural space of a spinal cord, comprising:
    a conformable substrate which is primarily composed of a flexible and stretchable polymer;
    a plurality of flexible and stretchable electrodes and stretchable conductive leads embedded in the conformable substrate; and
    microfluidic channels that are embedded in the conformable substrate, wherein the electrical and pharmaceutical stimulation is applied to the spinal cord, epidurally or subdurally,
    wherein the stretchable conductive leads are essentially made of a polymer matrix with an electrically conductive filler material, wherein the filler material is at least one of Ag, Au, Cu, Pt, Ir, Al, Fe, Cr, Ni, C, In, Sn, and Ti; and
    wherein the filler material is present in fibrous, particle, or nanotube form, further configured such that pharmaceuticals to the epidural or subdural space can be delivered through the microfluidic channels.

2. The device according to claim 1, wherein at least one of the electrodes and leads are stretchable by at least 20% while maintaining their conductivity.

3. The device according to claim 1, wherein the conformable substrate essentially consists of poly(dimethylsiloxane).

4. The device according to claim 3, wherein at least one of the electrodes and leads essentially consist of conductive poly(dimethylsiloxane).

5. The device according to claim 1, further comprising at least one of the following:
- a reception means for contactless energy supply to the plurality of flexible and stretchable electrodes;
- an electrical circuit embedded in the conformable substrate or attached to the conformable substrate; or
- a battery configured to supply electricity to the plurality of flexible and stretchable electrodes.

6. The device according to claim 1, having a total thickness of less than 1 mm.

7. The device according to claim 1, wherein at least one of the electrodes and conductive leads is functionalized with a drug releasing coating.

8. The device according to claim 1, further comprising a plurality of holes or other microstructures to improve fluid circulation and thermoregulation and/or to promote tissue ingrowth and/or to prevent inflammation when the device is implanted.

9. The device according to claim 1, wherein the electrodes form a multi-electrode array for stimulating neural tissue.

10. The device of claim 1, wherein at least one of the electrodes and leads are stretchable by more than 50% while maintaining their conductivity.

11. The device of claim 1, wherein the microfluidic channels embedded in the conformable substrate are horizontal channels.

12. The device of claim 1, wherein a first layer of the conformable substrate is non-conducting.

13. A method of neurostimulation, comprising:
implanting a device in an epidural or subdural space of a spinal cord of an animal or human, the device comprising:
- a conformable substrate which is primarily composed of a flexible and stretchable polymer; and
- a plurality of flexible and stretchable electrodes and stretchable conductive leads embedded in the conformable substrate, wherein the stretchable conductive leads are essentially made of a polymer matrix with an electrically conductive filler material, wherein the filler material is at least one of Ag, Au, Cu, Pt, Ir, Al, Fe, Cr, Ni, C, In, Sn, and Ti; and
wherein the filler material is present in fibrous, particle, or nanotube form, further configured such that drugs to the epidural or subdural space can be delivered through microfluidic channels embedded within the device;
the method further comprising:
stimulating neurons in the spinal cord by providing electrical signals to the electrodes or the conductive leads of the device configured and arranged for implantation in the epidural or subdural space of the spinal cord.

14. A method of drug delivery, comprising:
implanting a device in an epidural or subdural space of a spinal cord of an animal or human, the device comprising:
- a conformable substrate which is primarily composed of a flexible and stretchable polymer; and
- a plurality of flexible and stretchable electrodes and stretchable conductive leads embedded in the conformable substrate, wherein the stretchable conductive leads are essentially made of a polymer matrix with an electrically conductive filler material, wherein the filler material is at least one of Ag, Au, Cu, Pt, Ir, Al, Fe, Cr, Ni, C, In, Sn, and Ti; and
wherein the filler material is present in fibrous, particle, or nanotube form, further configured such that drugs to the epidural or subdural space can be delivered through microfluidic channels embedded within the device;
the method further comprising:
delivering drugs to the epidural or subdural space through the microfluidic channels embedded within the device.

15. A method of recording neuronal signals, comprising:
implanting a device in an epidural or subdural space of a spinal cord of an animal or human, the device comprising:
- a conformable substrate which is primarily composed of a flexible and stretchable polymer; and
- a plurality of flexible and stretchable electrodes and stretchable conductive leads embedded in the conformable substrate, wherein the stretchable conductive leads are essentially made of a polymer matrix with an electrically conductive filler material, wherein the filler material is at least one of Ag, Au, Cu, Pt, Ir, Al, Fe, Cr, Ni, C, In, Sn, and Ti; and
wherein the filler material is present in fibrous, particle, or nanotube form, further configured such that drugs to the epidural or subdural space can be delivered through microfluidic channels embedded within the device;
the method further comprising:
recording neuronal signals from the spinal cord received by the electrodes or the conductive leads of the device.

* * * * *